(12) United States Patent
Maini

(10) Patent No.: US 11,660,121 B2
(45) Date of Patent: May 30, 2023

(54) TRANSSEPTAL INSERTION DEVICE

(71) Applicant: Brijeshwar S. Maini, West Palm Beach, FL (US)

(72) Inventor: Brijeshwar S. Maini, West Palm Beach, FL (US)

(73) Assignee: East End Medical LLC, Lewes, DE (US)

( * ) Notice: Subject to any disclaimer, the term of this patent is extended or adjusted under 35 U.S.C. 154(b) by 45 days.

(21) Appl. No.: 15/784,792

(22) Filed: Oct. 16, 2017

(65) Prior Publication Data
US 2018/0103985 A1   Apr. 19, 2018

Related U.S. Application Data

(60) Provisional application No. 62/409,448, filed on Oct. 18, 2016.

(51) Int. Cl.
*A61B 17/34* (2006.01)
*A61B 18/14* (2006.01)
(Continued)

(52) U.S. Cl.
CPC ........ *A61B 17/50* (2013.01); *A61B 17/00234* (2013.01); *A61B 17/3403* (2013.01);
(Continued)

(58) Field of Classification Search
CPC ........... A61B 2017/00247; A61B 2017/00557; A61B 2017/320052; A61B 2017/320056;
(Continued)

(56) References Cited

U.S. PATENT DOCUMENTS 4,696,304 A   9/1987   Chin
4,813,934 A   3/1989   Engelson et al.
(Continued)

FOREIGN PATENT DOCUMENTS

AU   2018307956 A1   2/2020
AU   2018307969 A1   2/2020
(Continued)

OTHER PUBLICATIONS

International Search Report PCT/US2017/056843 Completed: Nov. 20, 2017; dated Dec. 14, 2017 4 pages.
(Continued)

*Primary Examiner* — Ronald Hupczey, Jr.
*Assistant Examiner* — Bradford C. Blaise
(74) *Attorney, Agent, or Firm* — FisherBroyles, LLP; Rachel H. Huffstetler

(57) ABSTRACT

A transseptal insertion device is provided including device housing, a pusher slidably disposed in the device housing and a guide element extending from the pusher. The device housing is configured to be inserted into the right atrium of a patient's heart and the guide element can then be advanced from the device housing and against the cardiac septum to facilitate stable puncturing of the cardiac septum by a needle carried by a catheter inserted through the device housing, to provide access to the left atrium. The guide element can be formed as a webbing or ring. The pusher and/or guide element can optionally be inflatable.

13 Claims, 11 Drawing Sheets

(51) Int. Cl.
  *A61B 17/00* (2006.01)
  *A61B 18/00* (2006.01)
  *A61B 17/50* (2006.01)
  *A61B 17/52* (2006.01)
  *A61B 90/00* (2016.01)

(52) U.S. Cl.
  CPC ...... *A61B 17/3468* (2013.01); *A61B 17/3478* (2013.01); *A61B 17/52* (2013.01); *A61B 18/14* (2013.01); *A61B 18/1492* (2013.01); *A61B 2017/00247* (2013.01); *A61B 2017/00557* (2013.01); *A61B 2017/3413* (2013.01); *A61B 2017/3482* (2013.01); *A61B 2018/00273* (2013.01); *A61B 2018/00369* (2013.01); *A61B 2018/00577* (2013.01); *A61B 2090/036* (2016.02)

(58) Field of Classification Search
  CPC .... A61B 2017/3405; A61B 2017/3409; A61B 2017/3482; A61B 17/34; A61B 17/3403; A61B 17/3415; A61B 17/3468; A61B 17/3478; A61B 17/50; A61B 2018/00273; A61B 2018/00351; A61B 2018/00577; A61B 18/1477; A61B 18/1492; A61B 2090/036
  See application file for complete search history.

(56) References Cited

U.S. PATENT DOCUMENTS

| | | | |
|---|---|---|---|
| 5,135,001 | A | 8/1992 | Sinofsky et al. |
| 5,295,958 | A | 3/1994 | Shturman |
| 5,699,805 | A | 12/1997 | Seward et al. |
| 5,792,118 | A | 11/1998 | Kurth et al. |
| 5,865,801 | A | 2/1999 | Houser |
| 6,017,323 | A | 1/2000 | Chee |
| 6,102,907 | A | 8/2000 | Smethers et al. |
| 6,102,926 | A | 8/2000 | Targalia et al. |
| 6,129,672 | A | 10/2000 | Seward et al. |
| 6,231,588 | B1 | 5/2001 | Zadno-azizi |
| 6,440,097 | B1 | 8/2002 | Kupiecki |
| 6,540,712 | B1 | 4/2003 | Parodi et al. |
| 7,666,203 | B2 | 2/2010 | Chanduszko et al. |
| 7,678,081 | B2 | 3/2010 | Whiting et al. |
| 8,096,959 | B2 | 1/2012 | Stewart et al. |
| 8,900,214 | B2 | 12/2014 | Nance et al. |
| 9,072,872 | B2 | 7/2015 | Asleson et al. |
| 9,510,904 | B2 | 12/2016 | Krishnan |
| 9,545,265 | B2 | 1/2017 | Maisano et al. |
| 9,700,351 | B2 | 7/2017 | Maisano et al. |
| 9,757,137 | B2 | 9/2017 | Krolik et al. |
| 2003/0019546 | A1 | 1/2003 | Kanekiyo et al. |
| 2003/0023204 | A1 | 1/2003 | Vo et al. |
| 2003/0229386 | A1 | 12/2003 | Rosenman et al. |
| 2004/0215233 | A1 | 10/2004 | Kaplan et al. |
| 2005/0065419 | A1 | 3/2005 | Partridge et al. |
| 2005/0159738 | A1 | 7/2005 | Visram et al. |
| 2005/0197530 | A1 | 9/2005 | Wallace |
| 2005/0245822 | A1 | 11/2005 | Dala-Krishna et al. |
| 2006/0009715 | A1 | 1/2006 | Khairkhahan et al. |
| 2007/0149995 | A1 | 6/2007 | Quinn et al. |
| 2007/0270751 | A1 | 11/2007 | Stangenes et al. |
| 2007/0293724 | A1* | 12/2007 | Saadat ................ A61B 1/0008 600/156 |
| 2008/0132937 | A1 | 6/2008 | Hartley |
| 2008/0171989 | A1 | 7/2008 | Bell |
| 2008/0243081 | A1 | 10/2008 | Nance |
| 2008/0262596 | A1 | 10/2008 | Xiao |
| 2009/0076498 | A1 | 3/2009 | Saadat et al. |
| 2009/0259272 | A1 | 10/2009 | Reddy et al. |
| 2010/0010488 | A1 | 1/2010 | Kassab |
| 2010/0168777 | A1 | 7/2010 | Stangenes et al. |
| 2010/0174189 | A1 | 8/2010 | Abraham |
| 2010/0286718 | A1 | 11/2010 | Kassab |
| 2011/0270239 | A1 | 11/2011 | Werneth |
| 2011/0295268 | A1 | 12/2011 | Roelle |
| 2012/0203169 | A1 | 8/2012 | Tegg |
| 2012/0259263 | A1 | 10/2012 | Celermajer |
| 2013/0090649 | A1 | 4/2013 | Smith |
| 2013/0102862 | A1 | 4/2013 | Mercader |
| 2014/0039494 | A1 | 2/2014 | Kick et al. |
| 2014/0081301 | A1 | 3/2014 | Tran |
| 2014/0171903 | A1 | 6/2014 | Roman et al. |
| 2014/0276027 | A1 | 9/2014 | Gaddis |
| 2014/0309675 | A1 | 10/2014 | Maisano et al. |
| 2015/0165170 | A1 | 6/2015 | Beasley et al. |
| 2015/0173794 | A1* | 6/2015 | Kurth ................ A61M 25/09 600/585 |
| 2015/0217093 | A1 | 6/2015 | Tsutsui et al. |
| 2015/0216620 | A1 | 8/2015 | Davies et al. |
| 2015/0224240 | A1 | 8/2015 | Farnan et al. |
| 2015/0258270 | A1* | 9/2015 | Kunis ................ A61M 5/00 604/506 |
| 2015/0306359 | A1 | 10/2015 | Drasler |
| 2016/0008636 | A1 | 1/2016 | Warnking |
| 2016/0051321 | A1 | 2/2016 | Salahieh et al. |
| 2016/0081704 | A1* | 3/2016 | Jeon ................ A61B 17/221 606/128 |
| 2016/0100860 | A1 | 4/2016 | Lenker et al. |
| 2016/0143522 | A1 | 5/2016 | Ransbury et al. |
| 2016/0193449 | A1 | 7/2016 | Sarabia et al. |
| 2016/0279393 | A1 | 9/2016 | Anderson et al. |
| 2017/0105761 | A1 | 4/2017 | Sapir et al. |
| 2017/0135559 | A1 | 5/2017 | Horrisberger et al. |
| 2017/0143940 | A1 | 5/2017 | Flygare |
| 2018/0103985 | A1 | 4/2018 | Maini |
| 2018/0177516 | A1 | 6/2018 | Vardi |
| 2018/0264231 | A1 | 9/2018 | Scheibe et al. |
| 2019/0000544 | A1 | 1/2019 | Govari et al. |
| 2019/0029722 | A1 | 1/2019 | Maini |
| 2019/0029750 | A1 | 1/2019 | Maini |
| 2019/0134412 | A1 | 5/2019 | Shuros et al. |
| 2019/0209177 | A1 | 7/2019 | Whitfield et al. |
| 2020/0297412 | A1 | 9/2020 | Maini |
| 2020/0390495 | A1 | 12/2020 | Maini |
| 2021/0085384 | A1 | 3/2021 | Maini |
| 2021/0100981 | A1 | 8/2021 | Maini et al. |
| 2021/0251553 | A1 | 8/2021 | Maini |

FOREIGN PATENT DOCUMENTS

| | | |
|---|---|---|
| AU | 2020241992 A1 | 10/2021 |
| CA | 3041032 A1 | 4/2018 |
| CA | 3071391 A1 | 1/2019 |
| CA | 3071432 A1 | 1/2019 |
| CA | 3151548 A1 | 3/2021 |
| CL | 2019001078 A1 | 11/2019 |
| CL | 2020000232 A1 | 2/2021 |
| CN | 1599579 A | 3/2005 |
| CN | 101442946 A | 5/2009 |
| CN | 103429179 A | 12/2013 |
| CN | 107530532 A | 1/2018 |
| CN | 110022779 A | 7/2019 |
| CN | 111093539 A | 5/2020 |
| CN | 111148474 A | 5/2020 |
| CN | 114727804 A | 7/2022 |
| EP | 2233169 A1 | 9/2010 |
| EP | 2459266 A1 | 6/2012 |
| EP | 3658036 A1 | 3/2020 |
| EP | 3253438 B1 | 9/2022 |
| IN | 202017008345 A | 10/2020 |
| JP | H06506853 | 8/1994 |
| JP | H08117232 A | 5/1996 |
| JP | 2009539575 | 11/2009 |
| JP | 2013226429 A | 11/2013 |
| JP | 2020530372 A | 10/2020 |
| JP | 2020530373 A | 10/2020 |
| WO | 02/096264 A2 | 12/2002 |
| WO | 2007147060 A2 | 12/2007 |
| WO | 2014036317 A2 | 3/2014 |
| WO | 2015058007 A1 | 4/2015 |
| WO | 2017083785 | 5/2017 |

(56) References Cited

FOREIGN PATENT DOCUMENTS

| | | |
|---|---|---|
| WO | 2018033401 A1 | 2/2018 |
| WO | 2018075426 A1 | 4/2018 |
| WO | 2019023609 A1 | 1/2019 |
| WO | 2019023653 A1 | 1/2019 |
| WO | 2019113043 A1 | 6/2019 |
| WO | 2020191133 A1 | 9/2020 |
| WO | 2020251999 A1 | 12/2020 |
| WO | 2021055572 A1 | 3/2021 |

OTHER PUBLICATIONS

Written Opinion of the International Searching Authority PCT/US2017/056843 dated Dec. 14, 2017 6 pages.
International Search Report and Written Opinion for International Application No. PCT/US2018/044143 dated Dec. 5, 2018, 16 sheets.
International Search Report and Written Opinion for International Application No. PCT/US2018/044207 dated Oct. 31, 2018, 17 sheets.
International Search Report and Written Opinion for International Application No. PCT/US2020/023518 dated Jun. 23, 2020, 15 sheets.
The extended European search report dated May 12, 2020, from EP Application No. 17862286.6, 8 sheets.
International Search Report and Written Opinion for International Application No. PCT/US2020/036965 dated Sep. 16, 2020, 16 sheets.
Non-Final Office Action dated Apr. 30, 2021, from U.S. Appl. No. 16/047,910, 46 sheets.
International Search Report and Written Opinion for International Application No. PCT/US2020/051228 dated Dec. 1, 2020, 14 sheets.
Invitation to Respond to Written Opinion from Singapore Patent Application No. 11202000666S, dated Mar. 2, 2021, 11 sheets.
Invitation to Respond to Written Opinion from Singapore Patent Application No. 11202000667S, dated Mar. 2, 2021, 11 sheets.
First Office Action dated May 7, 2021, from Chinese Application No. 201780074077.5, 15 sheets.
Written Opinion dated Jun. 16, 2021, from Chilean Patent Application N° 202000403, 16 sheets.
International Search Report and Written Opinion dated May 25, 2021, from International Patent Application No. PCT/US2021/017528, 15 sheets.
International Search Report and Written Opinion dated Jan. 13, 2021, from PCT/US2020/53902, 12 sheets.
Communication Pursuant to Article 94(3) EPC dated Aug. 25, 2021, from EP Application No. 18755361.5, 4 sheets.
Office Action dated Sep. 3, 2021, from Chile Application No. 202000232, 20 sheets.
Notice of Reasons for Rejection dated Sep. 28, 2021, from Japanese Application No. 2019-521811, 4 sheets.
International Search Report and Written Opinion dated Oct. 1, 2021, from PCT Application No. PCT/US2021/018409, 17 sheets.
International Preliminary Report on Patentability PCT/US2017/056843; dated May 2, 2019, 5 pages.
International Preliminary Report on Patentability PCT/US2018/044207; dated Feb. 6, 2020, 8 pages.
International Preliminary Report on Patentability PCT/US2018/044143; dated Feb. 28, 2020, 9 pages.
International Preliminary Report on Patentability PCT/US2020/023518; dated Sep. 30, 2021, 10 pages.
International Preliminary Report on Patentability PCT/US2020/053902; dated Apr. 14, 2022, 5 pages.
International Preliminary Report on Patentability PCT/US2020/036965; dated Dec. 23, 2021, 8 pages.
International Preliminary Report on Patentability PCT/US2020/051228; dated Mar. 31, 2022, 9 pages.
EP Application No. 18756031.3, EP Communication dated Oct. 4, 2021, 11 pages.

* cited by examiner

TRANSSEPTAL INSERTION DEVICE

FIELD OF THE INVENTION

The present invention relates generally to cardiac catheters, and more particularly, to a transseptal insertion device which is suitable for facilitating quick and safe transseptal puncture and insertion of a needle or catheter through a cardiac septum to provide access to the left atrium in implementation of a left atrial intervention.

BACKGROUND OF THE INVENTION

Cardiac catheterization is a medical procedure in which a long thin tube or catheter is inserted through an artery or vein into specific areas of the heart for diagnostic or therapeutic purposes. More specifically, cardiac chambers, vessels and valves may be catheterized.

Cardiac catheterization may be used in procedures such as coronary angiography and left ventricular angiography. Coronary angiography facilitates visualization of the coronary vessels and finding of potential blockages by taking X-ray images of a patient who has received a dye (contrast material) injection into a catheter previously injected in an artery. Left ventricular angiography enables examination of the left-sided heart chambers and the function of the left-sided valves of the heart, and may be combined with coronary angiography. Cardiac catheterization can also be used to measure pressures throughout the four chambers of the heart and evaluate pressure differences across the major heart valves. In further applications, cardiac catheterization can be used to estimate the cardiac output, or volume of blood pumped by the heart per minute.

Some medical procedures may require catheterization into the left atrium of the heart. For this purpose, in order to avoid having to place a catheter in the aorta, access to the left atrium is generally achieved by accessing the right atrium, puncturing the interatrial septum between the left and right atria of the heart, and threading the catheter through the septum and into the left atrium. Transseptal puncture must be carried out with extreme precision, as accidental puncturing of surrounding tissue may cause very serious damage to the heart. In addition, transseptal puncture may require complicated instruments which are not helpful in guaranteeing the precision of the puncture.

Accordingly, there is an established need for a device that is suitable for facilitating quick and safe transseptal puncturing to provide access to the left atrium in implementation of a left atrial intervention.

SUMMARY OF THE INVENTION

It is an object of the present invention to provide a device that is suitable for facilitating quick and safe transseptal puncturing to provide access to the left atrium in implementation of a left atrial intervention.

The present invention is directed to a transseptal insertion device which is suitable for facilitating quick and safe transseptal insertion of a needle or catheter through an interatrial cardiac septum to provide access to the left atrium in implementation of a left atrial intervention. The transseptal insertion device is elongated yet has a relatively reduced length, and can be easily and safely turned within an atrium of the heart to achieve a correct orientation towards the cardiac septum.

Introducing a first implementation of the invention, the present invention includes a transseptal insertion device which is suitable for facilitating a precise and safe transseptal insertion of a needle or catheter through a cardiac septum, comprising a device housing and a slidable body slidably disposed in the device housing. The slidable body includes a pusher and a guide element extending from the pusher. The guide element us extendable and retractable from a distal end of the device housing.

In a second aspect, the guide element may be formed as a web.

In another aspect, the device housing may include a housing interior and an annular housing gap surrounding the housing interior, and the guide element may be slidably disposed within the housing gap.

In another aspect, the device housing may include an outer housing wall, an inner housing wall, a housing interior formed by the inner housing wall and an annular housing gap surrounding the housing interior.

In still another aspect, the pusher may include a front pusher ring, a rear pusher ring spaced-apart from the front pusher ring and at least one pusher rod extending between the front pusher ring and the rear pusher ring.

In yet another aspect, the one or more pusher rods may extend between the front pusher ring and the rear pusher ring.

In another aspect, the guide element may extend from the front pusher ring of the pusher.

In another aspect, the guide element may include multiple, parallel, spaced-apart longitudinal webbing elements and multiple, annular transverse webbing elements provided at spaced-apart intervals with respect to each other along the longitudinal webbing elements.

In another aspect, multiple anchors may terminate the respective longitudinal webbing elements of the guide element for impingement against the cardiac septum in insertion of a needle or catheter through an orifice in the septum.

In another aspect, at least one of the pusher and the guide element can be inflatable.

In another aspect, the device housing can include an outer housing wall defining a housing interior and a pusher channel extending through the outer housing wall generally parallel and adjacent to the housing interior. The guide element can further include a pusher having an inflatable pusher rod slidably disposed in the pusher channel and an inflatable pusher ring terminating and disposed in fluid communication with the pusher rod.

These and other objects, features, and advantages of the present invention will become more readily apparent from the attached drawings and the detailed description of the preferred embodiments, which follow Objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

DETAILED DESCRIPTION OF THE INVENTION

In the following description, numerous details are set forth for the purpose of example and explanation; however, one of ordinary skill in the art will realize that the invention may be practiced without the use of these specific details.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward a transseptal insertion device which is suitable for facilitating quick and safe transseptal puncturing of an interatrial septum and insertion of a catheter therethrough to provide access to the left atrium in implementation of a left atrial intervention.

Figure 2:
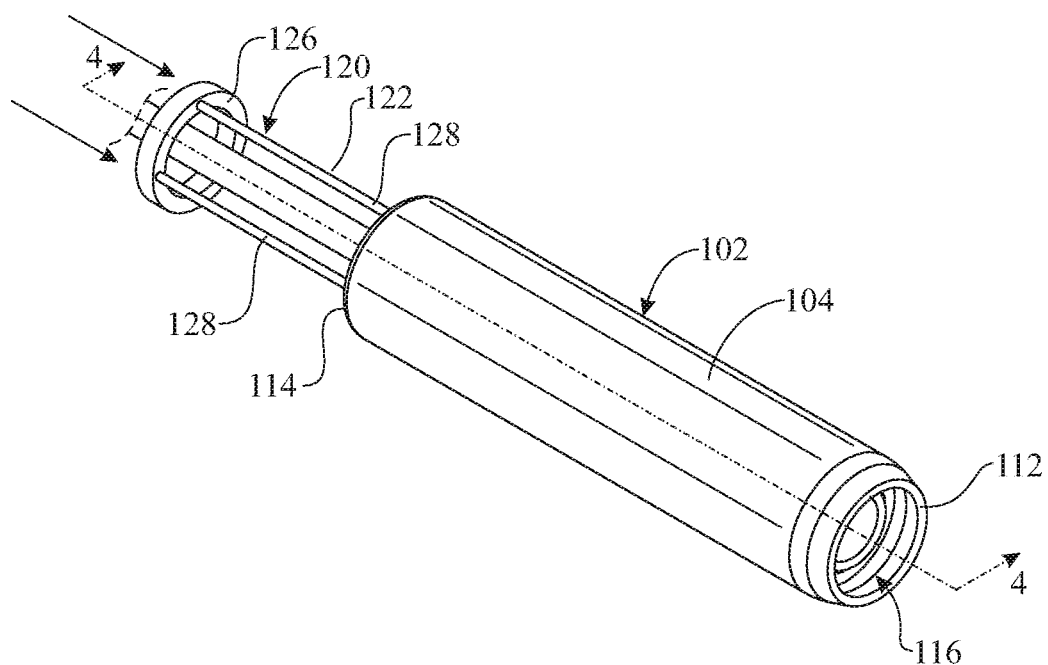
FIG. 2 presents a front perspective view of the transseptal insertion device of FIG. 1 in a first, retracted position, with the catheter extending partially through the device.
Figure 3:
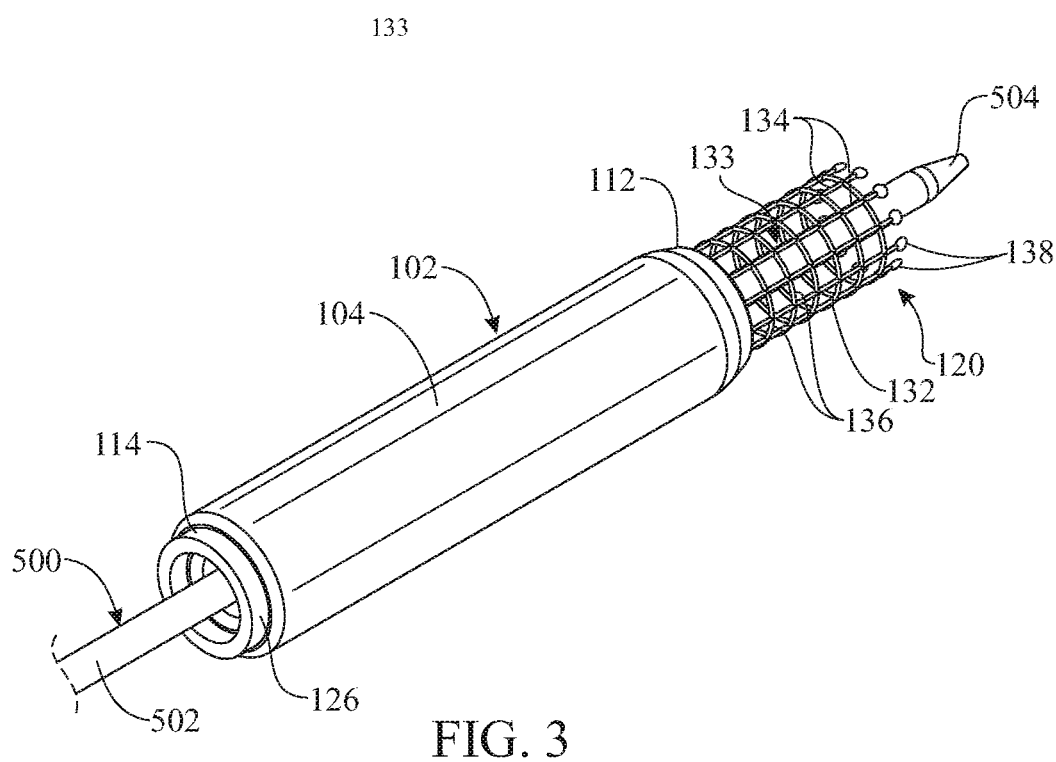
FIG. 3 presents a rear perspective view of the transseptal insertion device of FIG. 1 in a second, advanced position, with the catheter extending through the device and protruding distally from the device.
Figure 4:
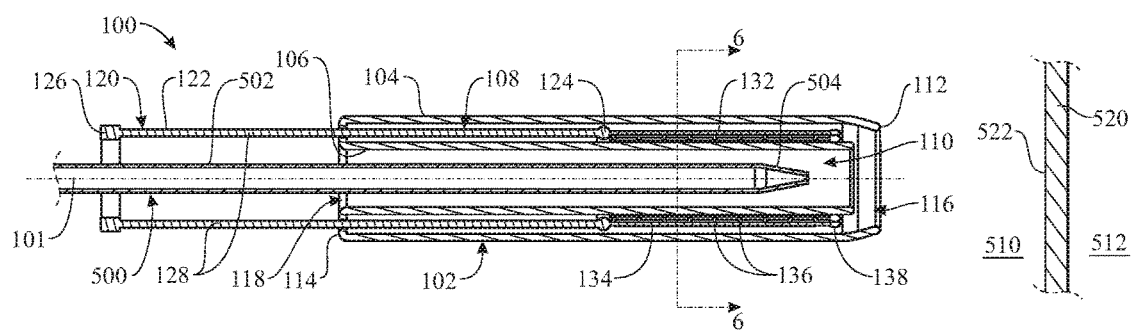
FIG. 4 presents a cross-sectional view of the transseptal insertion device and catheter of FIG. 1 prior to puncturing an interatrial cardiac septum, the transseptal insertion device and catheter shown in the first, retracted position of FIG. 2, the cross section taken along section plane 4-4 indicated in FIG. 2.
Figure 5:
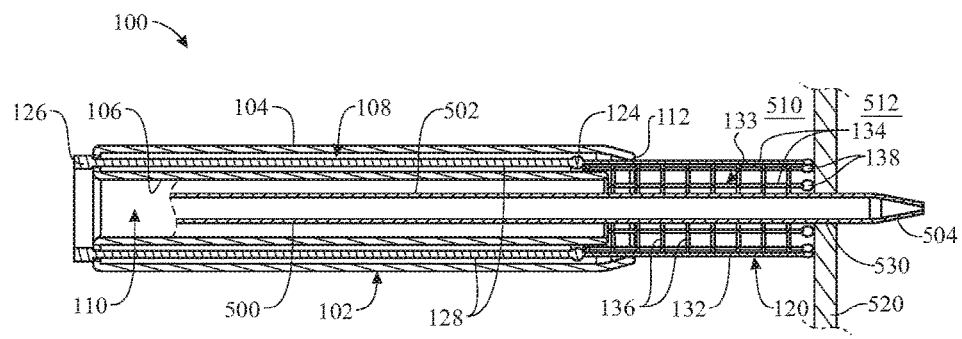
FIG. 5 presents a similar cross-sectional view of the transseptal insertion device and catheter of FIG. 1, the interatrial cardiac septum shown punctured, the transseptal insertion device shown in the second, advanced position of FIG. 3, and the catheter shown extending through the cardiac septum.
Figure 6:
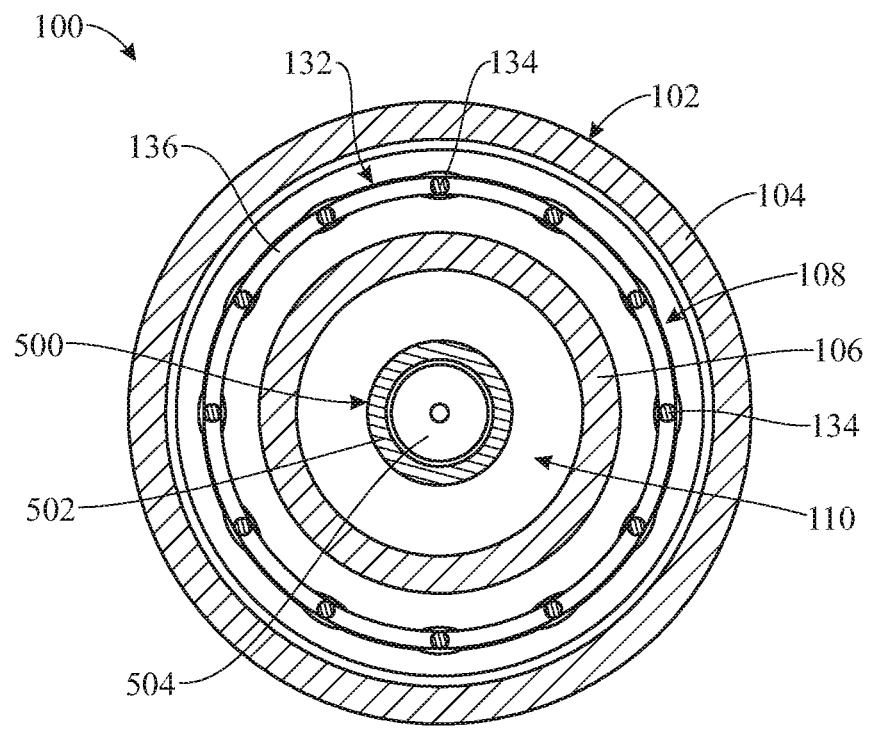
FIG. 6 is a cross-sectional view, taken along section plane 6-6 indicated in FIG. 4.

Referring initially to FIGS. 1-6, a transseptal insertion device 100 is illustrated in accordance with an exemplary embodiment of the present invention. As shown, the transseptal insertion device 100 is generally elongated and arranged along a longitudinal axis 101. The transseptal insertion device 100 may include a device housing 102. The device housing 102 may be generally elongated and cylindrical in shape arranged about the longitudinal axis 101, with an outer housing wall 104 and an inner housing wall 106 (FIGS. 4-6). The inner housing wall 106 may be generally parallel to and concentric with the outer housing wall 104 and about the longitudinal axis 101. An annular housing gap 108 may be formed by and between the outer housing wall 104 and the inner housing wall 106. A housing interior 110 may be formed by and within the inner housing wall 106. The device housing 102 may have a distal end 112 and a proximal end 114. In some embodiments, the distal end 112 of the device housing 102 may be tapered in longitudinal cross-section, as best shown in FIGS. 4 and 5. A front housing opening 116 may be disposed in communication with the housing gap 108 and the housing interior 110 at the distal end 112 of the device housing 102. A rear housing opening 118 may be disposed in communication with the housing interior 110 at the proximal end 114 of the device housing 102.

Further, the transseptal insertion device 100 includes a slidable body 120 which is arranged inside the device housing 102 and slidably or longitudinally translatable relative to the device housing 102. The slidable body 120 of the present embodiment is composed of a pusher 122 and a webbed guide element 132. In some embodiments, the slidable body 120, such as the pusher 122 and webbed guide element 132, can be formed into a single-piece unit such as by injection molding, welding or the like.

In certain embodiments, the slidable body 120 is covered with fabric such as PTFE/Dacron which makes it non-porous.

Figure 1:
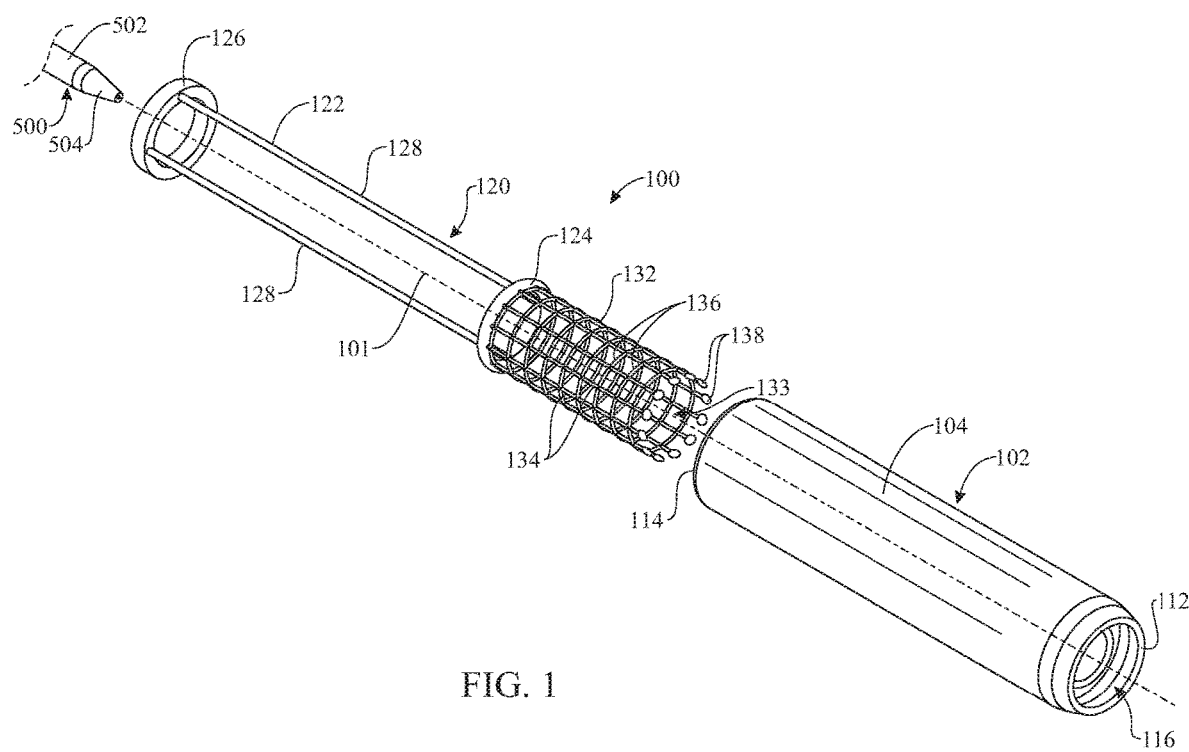
FIG. 1 presents a front perspective view of a transseptal insertion device in accordance with a first embodiment of the present invention, the device shown exploded and accompanied by a catheter.

As best shown in FIG. 1, the pusher 122 is slidably disposed within the housing gap 108 between the outer housing wall 104 and the inner housing wall 106 of the device housing 102. In some embodiments, the pusher 122 may include a front pusher ring 124 and a rear pusher ring 126 which is spaced-apart from the front pusher ring 124. At least one elongated pusher rod 128 may extend between the front pusher ring 124 and the rear pusher ring 126. In some embodiments, multiple pusher rods 128 may extend between the front pusher ring 124 and the rear pusher ring 126 in generally parallel relationship to each other around the circumference of the front pusher ring 124 and the rear pusher ring 126.

With continued reference to FIG. 1, the webbed guide element 132 extends forwardly from the pusher 122, such as from the front pusher ring 124 of the pusher 122. The webbed guide element 132 delimits an internal space 133 transversely, in order to provide a guiding effect of a needle or catheter traveling longitudinally trough the internal space 133, as will be explained in greater detail hereinafter. The webbed guide element 132 may be generally elongated and cylindrical in shape, as shown. In some embodiments, the webbed guide element 132 may be transversely expandable and/or retractable, i.e. allow for a variation of its diameter; for instance, the webbed guide element 132 may be expandable to a conical shape according to which a distal end of the webbed guide element 132 would have a larger diameter than a proximal end of the webbed guide element 132. Should the webbed guide element 132 be expandable, expansion is limited to a certain extent in order for the webbed guide element 132 to still provide the aforementioned guiding effect. In some embodiments, as shown in the present drawing, the webbed guide element 132 can include multiple, parallel longitudinal webbing elements 134 which are disposed in spaced-apart relationship to each other around the circumference of the webbed guide element 132; in turn, multiple, parallel, spaced-apart transverse webbing elements 136 may connect the longitudinal webbing elements 134 to each other in the webbed guide element 132. Alternative embodiments are contemplated, however, in which the construction of the webbed guide element 132 may vary; for instance, and without limitation, the webbed guide element can be made of oblique messing elements forming a net. The webbed guide element 132 can be made of nitinol, for instance and without limitation. In some embodiments, as shown in the present illustrations, widened sections or anchors 138 may terminate the distal ends of the respective longitudinal webbing elements 134 of the webbed guide element 132. The anchors 138 can be arranged around a perimeter of the webbed guide element 132 and substantially coplanar to one another on a plane that is transverse to the longitudinal axis 101 of the transseptal insertion device 100. The anchors 138 can be made of tantalum, for instance and without limitation.

As shown in FIGS. 2 and 3, the slidable body 120 can slidably adopt different longitudinal positions within the device housing 102. In a first or retracted position, shown in FIG. 2, the slidable body 120 is retracted relative to the device housing 102 so that the webbed guide element 132 is located generally inside the device housing 102 and the pusher 122 is protruding rearwardly from the proximal end 114 of the device housing 102. In a second or advanced position, the slidable body 120 is moved forward relative to the device housing 102 so that the slidable body 120 advances through the front housing opening 116 and protrudes outwardly from the distal end 112 of the device housing 102, the webbed guide element 132 extends outwardly and distally from the device housing 102 and the pusher 122 is generally received within the device housing 102. More specifically, in the second, advanced position, the pusher rods 128 can be received within the device housing 102, as shown, while the rear pusher ring 126 of the pusher 122 remains outside the device housing 102 and rests on the proximal end 114 of the device housing 102 to block the slidable body 120 from further advancing forward through the device housing 102.

For purposes that will be described hereinafter, the slidable body is used to anchor into the left atrial appendage in the eventuality of a perforation during a left atrial appendage procedure. Since it is non-porous, it will act as an occlusion balloon and prevent further extravasation of blood in the pericardial sac till a more definitive procedure may be performed or the bleeding stops For purposes that will be described hereinafter, a catheter 500 carrying a spear or needle can be inserted through the transseptal insertion device 100 and, guided by the slidable body 120, protrude outwardly from the distal end 112 of the device housing 102 as shown in FIG. 3.

In certain embodiments, the slidable body is used to remove an implanted mitral regulation (Mitraclip®) device. The slidable body is used to anchor onto the anterior and posterior leaflets of the mitral valve. Once anchored, there is either a mechanical, magnetic or electromagnetic lever that attaches to the mitral regulation device and stabilizes it. Energy is then delivered to the mitral valve to via the slidable body 120 to ablate the anterior and posterior leaflets. The mitral regulation device is thereby released and removed from the body. The slidable body 120 may also be used in the absence of a mitral regulation device on the mitral valve and may be used to ablate the anterior mitral leaflet prior to mitral valve implantation to prevent left ventricular outflow tract obstruction. In this instance, the anterior mitral leaflet would be stabilized with a set of stabilizers which would be housed within the slidable body 120. The stabilizers would be used to stabilize the anterior mitral leaflet first and then the slidable body would be used to deliver energy to ablate the anterior mitral leaflet. The ablated tissue would then be removed from the body using the stabilizer.

In certain embodiments, the slidable body is used to anchor into the pulmonary veins. Radiofrequency energy or other forms of energy may be delivered via the cable and the slidable body to the pulmonary veins to result in electrical ablation.

A typical application of the transseptal insertion device 100 to puncture the interatrial cardiac septum 520 is now described with reference to FIGS. 4 and 5.

Initially, the transseptal insertion device 100 is arranged in the retracted or first position (described heretofore with reference to FIG. 2) in which the slidable body 120 is retracted relative to the device housing 102 and the distal end 112 of the device housing 102 provides a tapered, front or distal end of the transseptal insertion device 100. The transseptal insertion device 100 is then inserted into the right atrium 510 of the heart through a catheter (hereinafter be referred to as "external catheter" for clarity purposes) extending through a vein; the external catheter and the vein are not shown in the drawings so as not to obscure the invention.

Once the transseptal insertion device 100 reaches the right atrium 510, a second, separate catheter 500 carrying a spear or needle (not shown) therewithin is extended through the slidable body 120 and the housing interior 110 of the device housing 102. The catheter 500 may have a conventional design with an elongated, typically flexible catheter body 502 and a tapered catheter tip 504 which terminates the catheter body 502. Before or after inserting the second, separate catheter 500 into the transseptal insertion device 100, the surgeon slowly moves the transseptal insertion device 100 to place it near, and facing, a target point 522 or area of the cardiac septum 520 to be punctured, as shown in FIG. 4.

Once the transseptal insertion device 100 is arranged facing the target point 522 of the cardiac septum 520, the transseptal insertion device 100 is operated to switch from the retracted position of FIG. 2 to the advanced position of FIG. 3; in other words, the slidable body 120 is pushed forward relative to the device housing 102 so that the webbed guide element 132 protrudes distally from the distal end 112 of the device housing 102. The transseptal insertion device 100 is arranged sufficiently close to the cardiac septum 520; thus, by pushing the slidable body 120 forward, the webbed guide element 132 eventually touches and rests on the cardiac septum 520. If present, the anchors 138 can engage the cardiac septum 520 to contribute to stabilize the webbed guide element 132 onto the cardiac septum 520 so that the webbed guide element 132 remains around the target point 522.

Once the webbed guide element 132 rests on the cardiac septum 520, the webbed guide element 132 and cardiac septum 520 enclose the internal space 133 of the webbed guide element 132 and the target point 522 of the cardiac septum 520. The spear or needle may then be advanced through the catheter 500 and towards the cardiac septum 520, puncturing the cardiac septum 520 and forming an orifice 530 in the cardiac septum 520. The slidable body 120 being arranged in the housing gap 108 between the outer housing wall 104 and the inner housing wall 106 of the device housing 102 contributes to stabilize the slidable body 120, and thus to maintain the webbed guide element 132 in a same position, providing a safe and precise aim when puncturing the cardiac septum 520.

Having created an orifice 530 in the cardiac septum 520, the catheter 500 may then be inserted through the orifice 530 and into the left atrium 512 of the patient's heart in order to proceed with the left atrium intervention as known in the art. The transseptal insertion device 100 may be maintained in the position of FIG. 5 to stabilize the catheter 500 and maintain its correct orientation relative to the cardiac septum 520.

After the cardiac catheterization procedures are completed, the catheter 500 may be withdrawn from the left atrium 512 through the orifice 530 and retracted back into the webbed guide element 132. Next, the webbed guide element 132 may be withdrawn from engagement with the cardiac septum 520 and into the housing gap 108, as illustrated in FIG. 4. Finally, the transseptal insertion device 100 may be removed from the right atrium 510 through the external catheter.

It will be appreciated by those skilled in the art that the transseptal insertion device 100 facilitates safer and quicker insertion of the spear or needle and the catheter 500 through the cardiac septum 520, and thus, quicker and safer access to the left atrium 512, minimizing the risk of damaging surrounding tissue during insertion of the needle or catheter 500.

Figure 8:
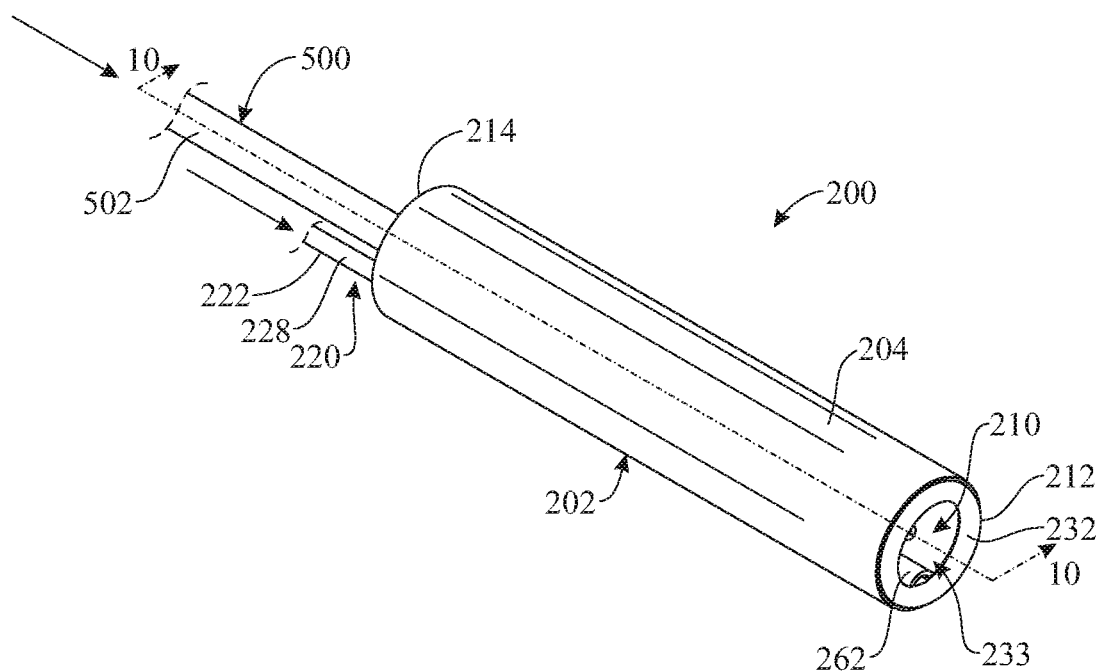
FIG. 8 presents a front perspective view of the transseptal insertion device of FIG. 7 in a first, retracted position, with the catheter extending partially through the device.
Figure 9:
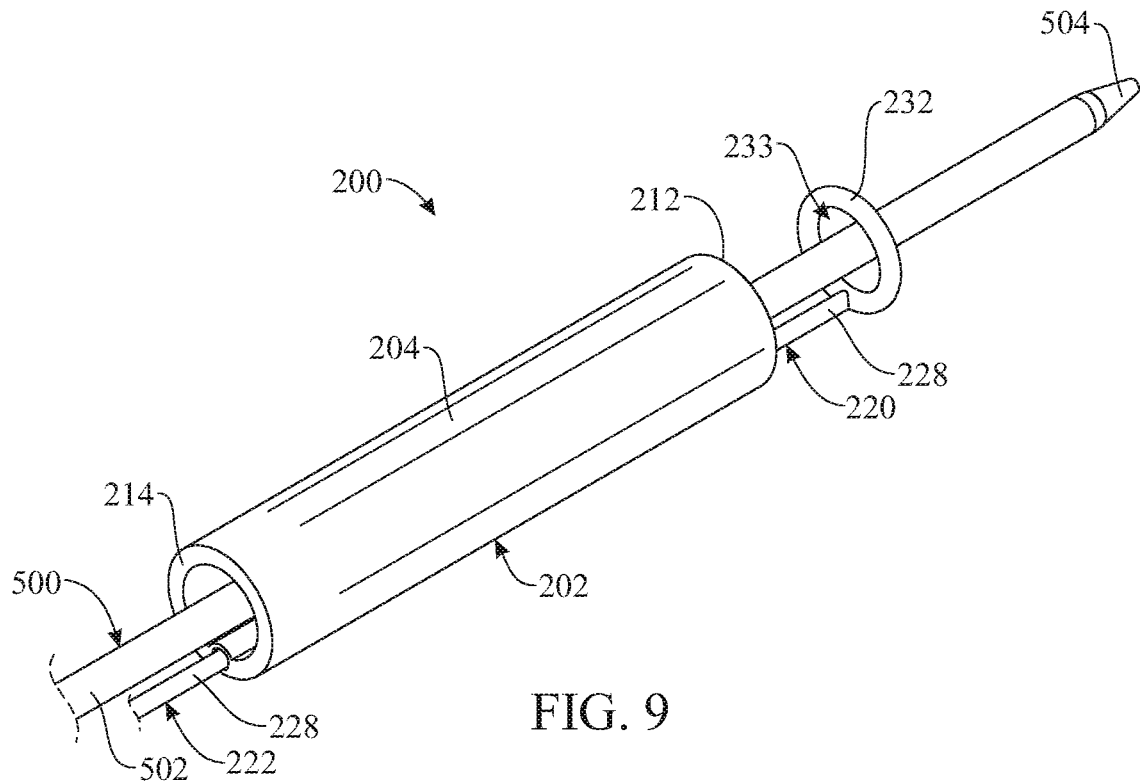
FIG. 9 presents a rear perspective view of the transseptal insertion device of FIG. 7 in a second, advanced position, with the catheter extending through the device and protruding distally from the device.
Figure 10:
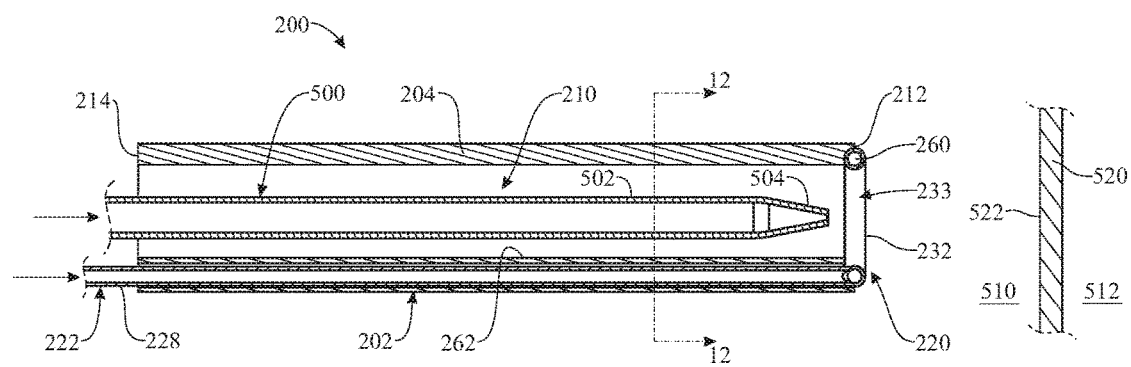
FIG. 10 presents a cross-sectional view of the transseptal insertion device and catheter of FIG. 7 prior to puncturing an interatrial cardiac septum, the transseptal insertion device and catheter shown in the first, retracted position of FIG. 8, the cross section taken along section plane 10-10 indicated in FIG. 8.
Figure 11:
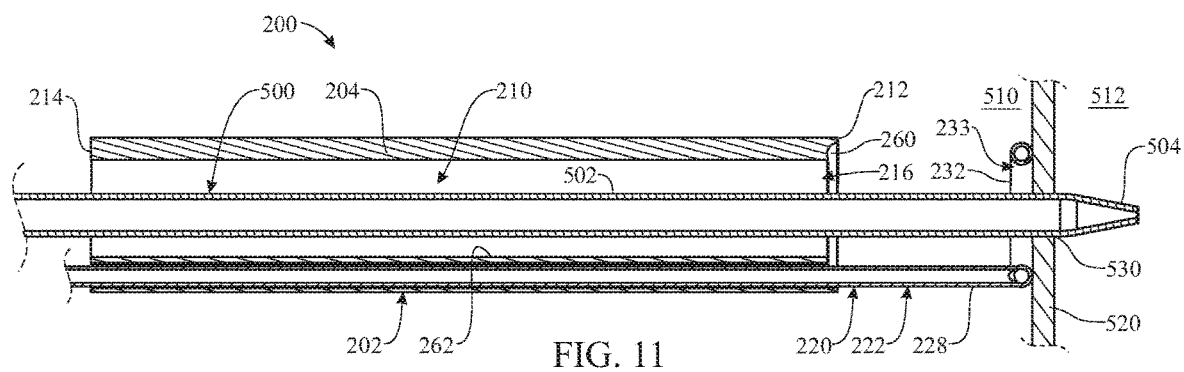
FIG. 11 presents a similar cross-sectional view of the transseptal insertion device and catheter of FIG. 7, the interatrial cardiac septum shown punctured, the transseptal insertion device shown in the second, advanced position of FIG. 9, and the catheter shown extending through the cardiac septum.
Figure 12:
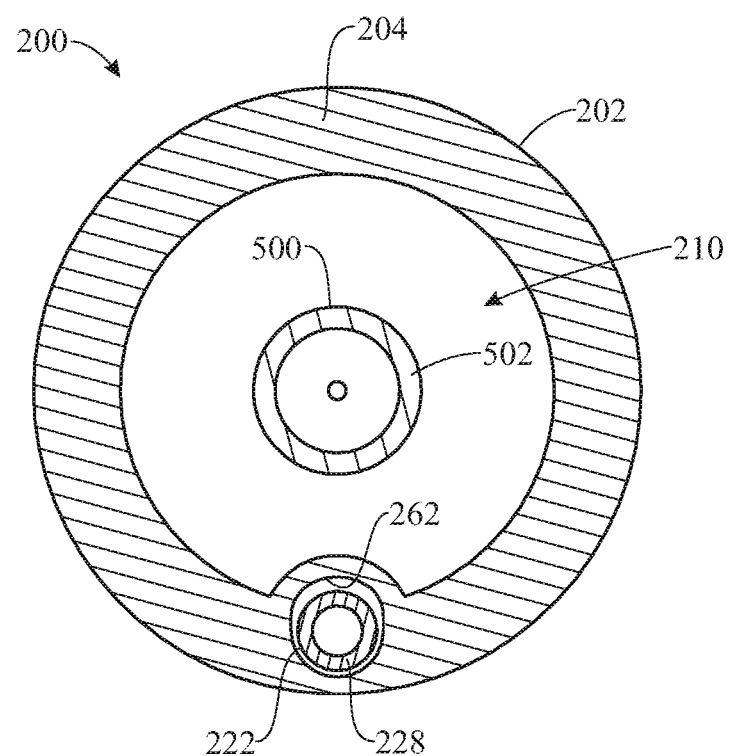
FIG. 12 is a cross-sectional view, taken along section plane 6-6 indicated in FIG. 10.

Referring next to FIGS. 7-12, a second illustrative embodiment of the transseptal insertion device is generally indicated by reference numeral 200. In the transseptal insertion device 200, elements which are analogous to the respective elements of the device 100 that was heretofore described with respect to FIGS. 1-6 are designated by the same respective numerals in the 200-299 series in FIGS. 7-12. Unlike the previous device housing 102, the device housing 202 of the transseptal insertion device 200 of the present embodiment has a single housing wall 204. As illustrated in FIGS. 10 and 11, a pusher channel 262 extends through and along the housing wall 204 from the proximal end 214 to the distal end 212 of the device housing 202. As illustrated in FIG. 11, the distal end 212 of the device housing 202 may have a concave seating area 260 which encircles the front housing opening 216.

Figure 7:
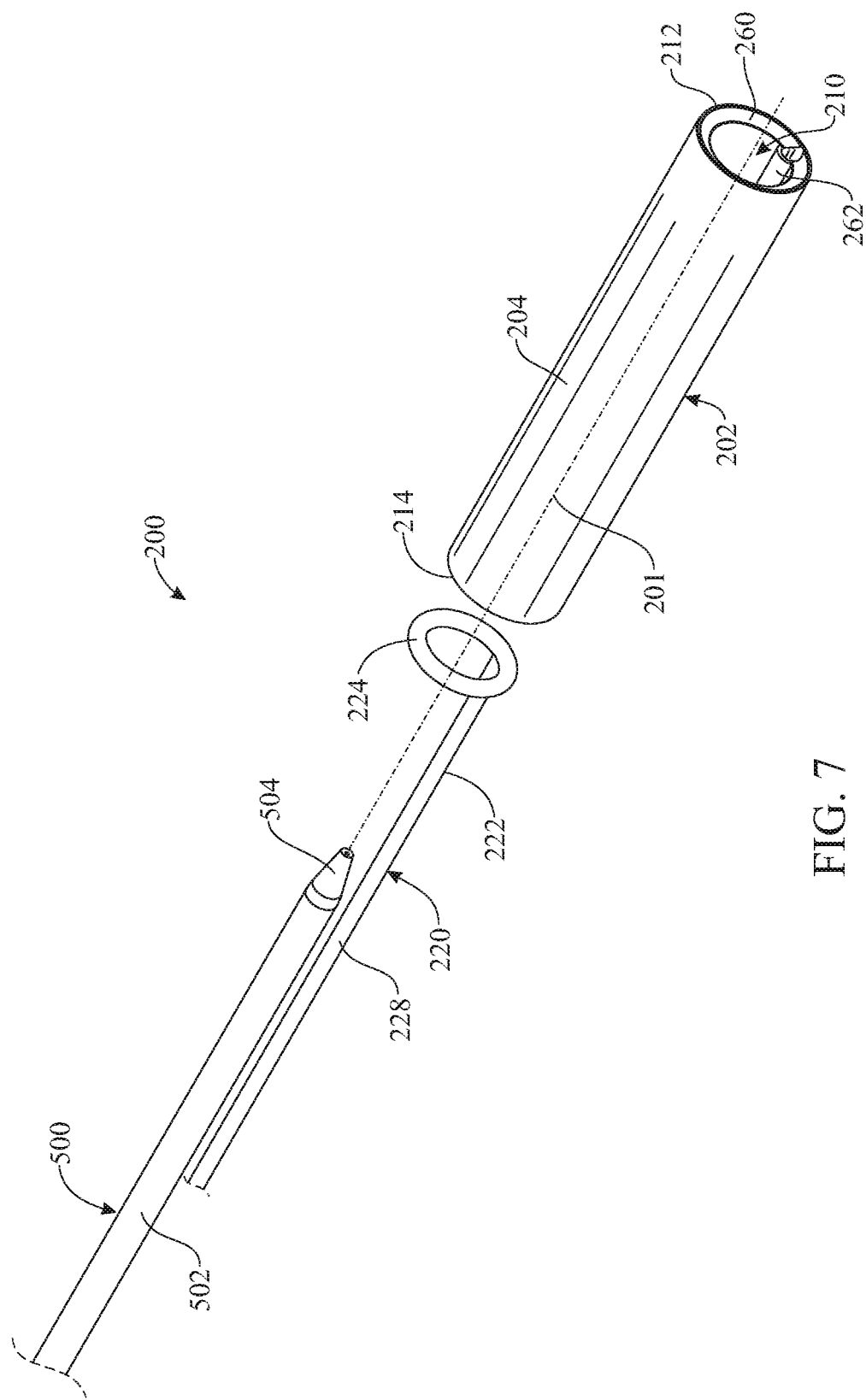
FIG. 7 presents a front perspective view of a transseptal insertion device in accordance with a second embodiment of the present invention, the device shown exploded and accompanied by a catheter

Similarly to the previous embodiment, as illustrated in FIGS. 7-9, the slidable body 220 of the present embodiment includes a pusher 222 and a guide element 232 extending from the pusher 222. The pusher 222 depicted herein consists of a single pusher rod 228. In turn, the guide element 232 is formed as a ring extending transversely from the pusher 222, the ring being shaped and sized to be received within the concave seating area 260 of the device housing 202. The slidable body 220 can be inflatable; for instance, and without limitation, the pusher rod 228 and the guide element 232 can be hollow, flexible and in fluid communication with one another. The pusher rod 228 is disposed for slidable displacement in the pusher channel 262 of the device housing 202. The pusher rod 228 may be disposed in fluid communication with an inflating fluid source (not illustrated) which introduces a supply of pressurized inflatable fluid (not illustrated) through the pusher rod 228 into the guide element 232 to inflate the pusher rod 228 and the guide element 232, for purposes which will be hereinafter described.

Similarly to the previous embodiment, as shown in FIGS. 8 and 9, the slidable body 220 of the present embodiment can slidably adopt different longitudinal positions within the device housing 202. In a first or retracted position, shown in FIG. 2, the slidable body 220 is retracted relative to the device housing 202 so that the annular guide element 232 is resting against the concave seating area 260 of the device housing 202. In a second or advanced position, the slidable body 220 is moved forward relative to the device housing 202 so that the pusher rod 228 advances through the pusher channel 262 of the device housing 202 and the slidable body 220 protrudes outwardly from the distal end 212 of the device housing 202, so that the guide element 232 is spaced apart from the distal end 212 of the device housing 212. A catheter 500 carrying a spear or needle can be inserted through the transseptal insertion device 200 and, guided by the annular guide element 232 of the slidable body 220, protrude outwardly from the distal end 212 of the device housing 202 as shown in FIG. 9.

A typical application of the transseptal insertion device 200 to puncture the interatrial cardiac septum 520 is now described with reference to FIGS. 10 and 11.

Initially, the transseptal insertion device 200 is arranged in the retracted or first position (described heretofore with reference to FIG. 8) in which the slidable body 220 is retracted relative to the device housing 202 and the distal end 212 of the device housing 202 together with the rounded annular guide element 232 provide a rounded, front or distal end of the transseptal insertion device 200. The transseptal insertion device 200 is then inserted into the right atrium 510 of the heart through a catheter (hereinafter be referred to as "external catheter" for clarity purposes) extending through a vein; the external catheter and the vein are not shown in the drawings so as not to obscure the invention.

Once the transseptal insertion device 200 reaches the right atrium 510, a second, separate catheter 500 carrying a spear or needle (not shown) therewithin is extended through the slidable body 220 and the housing interior 210 of the device housing 202. The catheter 500 may have a conventional design with an elongated, typically flexible catheter body 502 and a tapered catheter tip 504 which terminates the catheter body 502. Before or after inserting the second, separate catheter 500 into the transseptal insertion device 200, the surgeon slowly moves the transseptal insertion device 200 to place it near, and facing, a target point 522 or area of the cardiac septum 520 to be punctured, as shown in FIG. 10.

Once the transseptal insertion device 200 is arranged facing the target point 522 of the cardiac septum 520, the transseptal insertion device 200 is operated to switch from the retracted position of FIG. 8 to the advanced position of FIG. 9; in other words, the slidable body 220 is pushed forward relative to the device housing 202 so that the annular guide element 232 separates distally from the distal end 212 of the device housing 202. The transseptal insertion device 200 is arranged sufficiently close to the cardiac septum 520; thus, by pushing the slidable body 220 forward, the annular guide element 232 eventually touches and rests on the cardiac septum 520.

Once the annular guide element 232 rests on the cardiac septum 520, the annular guide element 232 and cardiac septum 520 enclose the internal space 233 of the webbed guide element 232 and the target point 522 of the cardiac septum 520. The spear or needle may then be advanced through the catheter 500 and towards the cardiac septum 520, puncturing the cardiac septum 520 and forming an orifice 530 in the cardiac septum 520.

Having created an orifice 530 in the cardiac septum 520, the catheter 500 may then be inserted through the orifice 530 and into the left atrium 512 of the patient's heart in order to proceed with the left atrium intervention as known in the art. The transseptal insertion device 200 may be maintained in the position of FIG. 11 to stabilize the catheter 500 and maintain its correct orientation relative to the cardiac septum 520.

After the cardiac catheterization procedures are completed, the catheter 500 may be withdrawn from the left atrium 512 through the orifice 530 and retracted back into the webbed guide element 232. Next, the annular guide element 232 may be withdrawn from engagement with the cardiac septum 520 and into the housing gap 208, as illustrated in FIG. 4. Finally, the transseptal insertion device 200 may be removed from the right atrium 510 through the external catheter.

Figure 13:
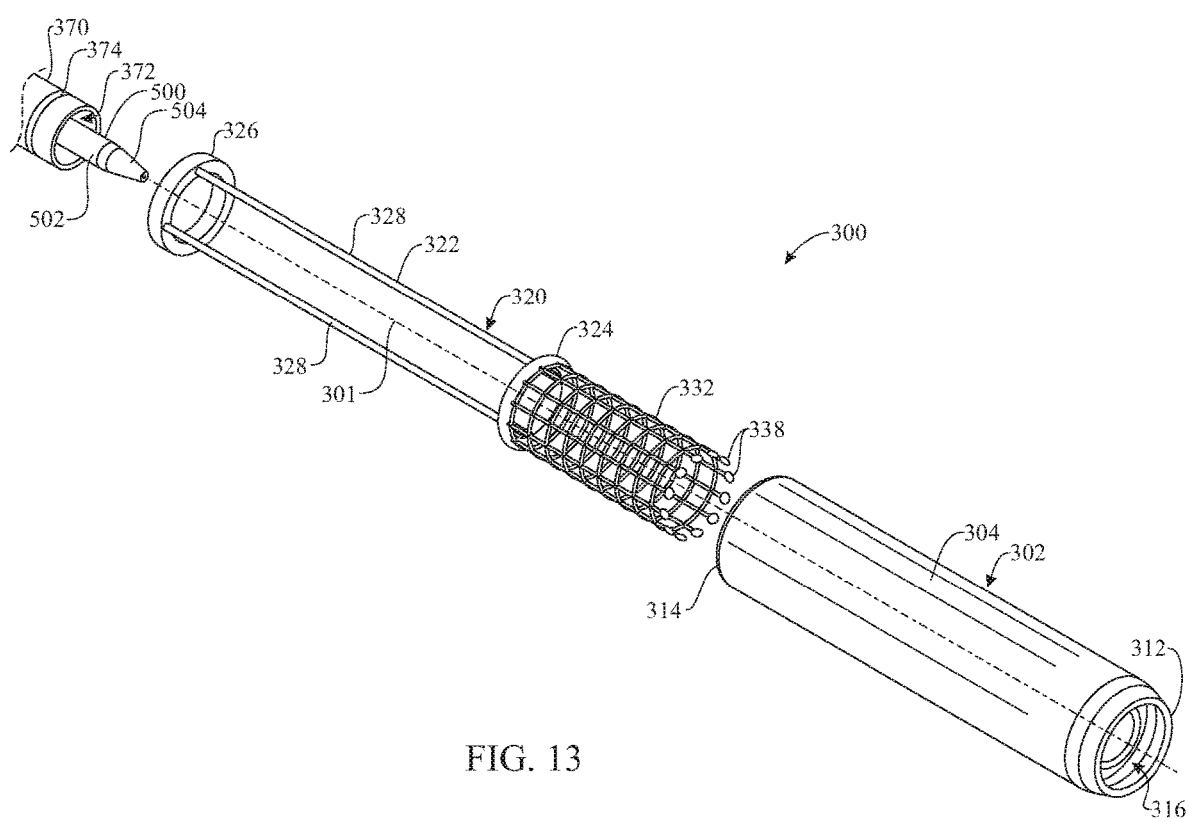
FIG. 13 presents a front perspective view of a transseptal insertion device in accordance with a third embodiment of the present invention, the device shown exploded and accompanied by a catheter.
Figure 14:
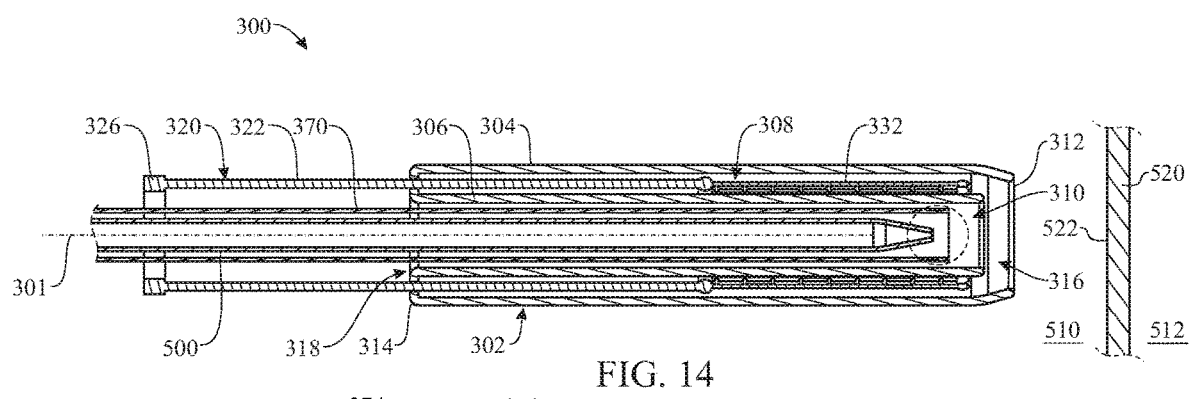
FIG. 14 presents a cross-sectional view of the transseptal insertion device and catheter of FIG. 13 prior to puncturing an interatrial cardiac septum, the transseptal insertion device and catheter shown in a retracted position.
Figure 15:
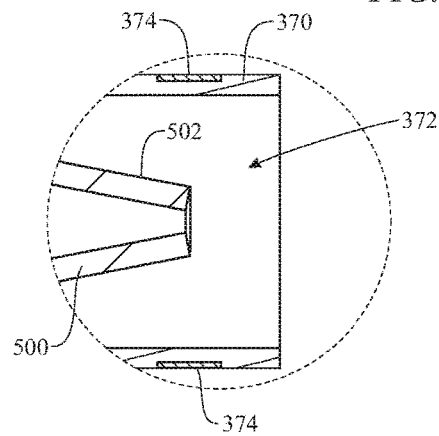
FIG. 15 presents an enlarged view of the distal end of the intermediate catheter of FIG. 14.

Referring next to FIGS. 13-15, a third illustrative embodiment of the transseptal insertion device is generally indicated by reference numeral 300. In the transseptal insertion device 300, elements which are analogous to the respective elements of the device 100 that was heretofore described with respect to FIGS. 1-6 are designated by the same respective numerals in the 300-399 series in FIGS. 13-15. The transseptal insertion device 300 of the present embodiment further includes an intermediate catheter 370 or thin tube comprising an internal space 372. As best shown in FIG. 14, the intermediate catheter 370 is arranged within the housing interior 310 of the device housing 302, between the inner housing wall 306 and the catheter 500. In other words, the intermediate catheter 370 is housed within the device housing 302 and in turn receives the catheter 500 intended to puncture and/or pass through the cardiac septum 520. As best shown in FIGS. 13 and 15, an outer, optionally annular ultrasound transducer 374 is carried by the intermediate catheter 370 at or near the distal end thereof. The intermediate catheter 370 can be extended outwardly and distally from the device housing 302 allowing for the ultrasound transducer 374 to capture ultrasound images of the surroundings of the transseptal insertion device 300 and facilitate a precise execution of the transseptal puncturing procedure.

In certain embodiments, the device includes a front-facing ultrasound transducer and/or a side-facing ultrasound transducer. In certain embodiments, the front-facing ultrasound transducer and/or a side-facing ultrasound transducer include a chip or ultrasound chip designed to convey and store electronic signals from the ultrasound transducer.

Figure 16:
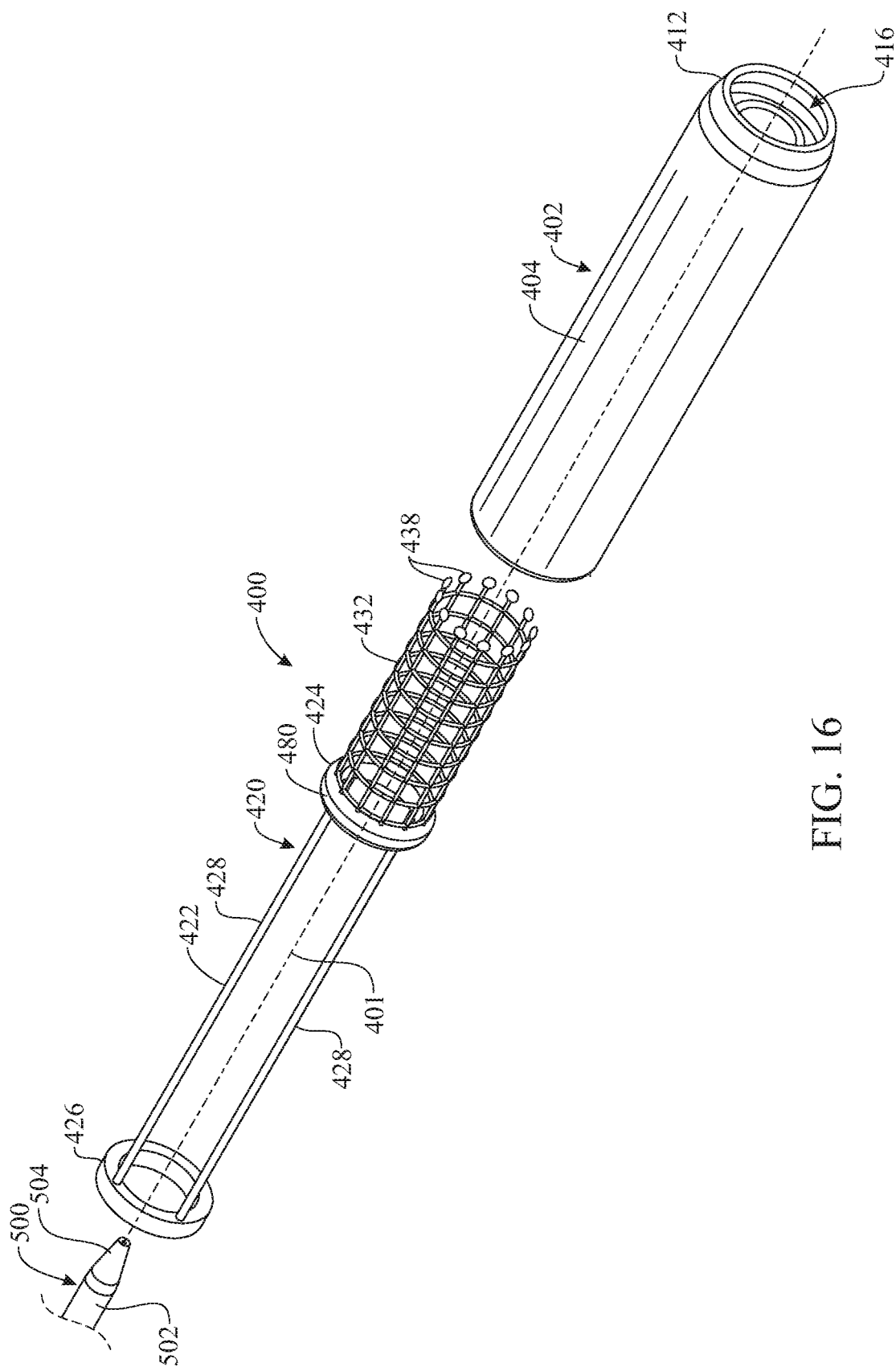
FIG. 16 presents a front perspective view of a transseptal insertion device in accordance with a fourth embodiment of the present invention, the device shown exploded and accompanied by a catheter Like reference numerals refer to like parts throughout the several views of the drawings.

Referring next to FIG. 16, a fourth illustrative embodiment of the transseptal insertion device is generally indicated by reference numeral 400. In the transseptal insertion device 400, elements which are analogous to the respective elements of the device 100 that was heretofore described with respect to FIGS. 1-6 are designated by the same respective numerals in the 400-499 series in FIG. 16. The transseptal insertion device 400 of the present embodiment further includes an optionally annular ultrasound transducer 474 carried by the slidable body 420, for instance by the front pusher ring 424 of the pusher 422. When the transseptal insertion device 400 is arranged in the advanced position, i.e. the slidable body 420 extends distally from the device housing 402, the ultrasound transducer 480 can capture ultrasound images of the surroundings of the transseptal insertion device 400 to facilitate a precise execution of the transseptal puncturing procedure.

The transseptal insertion device of the present invention can successfully assist the surgeon in carrying out at least one of the following techniques: visualization and stabilization of the intra atrial septum; visualization and stabilization of the fossa ovalis; guidance for transseptal puncture and across septum into safe zone of left atrium (away from structures such as aorta); guidance into the left atrium (for isolation of pulmonary veins for AFib ablation); visualization of the left atrium; guidance into the pulmonary veins; visualization and stabilization of the pulmonary veins, and more specifically of the ostium of the pulmonary veins; visualization and stabilization of the left atrial appendage; guidance into the left atrial appendage; visualization and stabilization of the mitral valve; and guidance into the mitral valve and left ventricle.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

The invention claimed is:

1. A transseptal insertion device for precise and safe transseptal insertion of a medical device through a cardiac septum comprising:
    a device housing having a distal end and a proximal end and including an outer wall and an inner wall wherein said inner wall and said outer wall are fixedly connected together and said inner wall and said outer wall are stationary relative to each other and said inner wall and said outer wall define an annular gap therebetween and wherein said inner wall defines a central lumen extending between said proximal and distal ends and wherein the medical device is received within said central lumen of said device housing;
    a slidable body positioned within said device housing annular gap, said slidable body having a distal end and a proximal end and defining a central lumen, configured to receive said device housing inner wall, said slidable body comprising a pusher and a guide element wherein said guide element is positioned on said slidable body distal end and said pusher extends within said device housing annular gap wherein said slidable body moves within said device housing annular gap from a first retracted position wherein at least a distal end of said pusher and said guide element are received within said device housing to a second advanced position wherein said guide element extends from said device housing distal end so as to contact the cardiac septum and wherein the medical device is configured to advance though said guide element for penetrating the cardiac septum.

2. The transseptal insertion device according to claim 1 wherein said device housing annular gap extends circumferentially within said device housing.

3. The transseptal insertion device according to claim 1 wherein a proximal end of said guide element is positioned within said device housing in said second advanced position.

4. The transseptal insertion device according to claim 1 wherein said guide element is a web comprising parallel, spaced apart longitudinal members and annular transverse members provided at spaced apart intervals with respect to each other wherein said longitudinal members and said transverse members define openings in said web.

5. The transseptal insertion device according to claim 1 wherein said guide element is expandable.

6. The transseptal insertion device according to claim 1 wherein said pusher comprises at least two pusher rods wherein said at least two pusher rods are radially displaced.

7. The transseptal insertion device according to claim 1 wherein said device housing distal end has a first diameter and said pusher has a second diameter in said second advanced position wherein said second diameter is greater than said first diameter.

8. The transseptal insertion device according to claim 1 wherein said medical device is a catheter.

9. The transseptal insertion device according to claim 1 wherein said guide element has a distal and proximal end and is expandable in said second advanced position to a conical shape wherein said distal end of said guide element is expanded relative to said proximal end of said guide element.

10. The transseptal insertion device according to claim 1 wherein said guide element further comprises at least one anchor on a distal end thereof for anchoring said guide element to the cardiac septum in said second advanced position.

11. The transseptal insertion device according to claim 1 wherein said device housing distal end is tapered.

12. The transseptal insertion device according to claim 1 further comprising an intermediate catheter configured for receipt of the medical device wherein said intermediate catheter is slidably positioned within said central lumen of said device housing.

13. The transseptal insertion device according to claim 1 wherein said slidable body includes an ultrasound transducer.

* * * * *